United States Patent
Buechter

(10) Patent No.: US 10,767,205 B2
(45) Date of Patent: Sep. 8, 2020

(54) BACTERIUM FOR THE PRODUCTION OF AN EXOPOLYSACCHARIDE COMPRISING N-ACETYLGLUCOSAMINE AND D-GLUCOSE

(71) Applicant: DePuy Synthes Products, Inc., Raynham, MA (US)

(72) Inventor: Douglas D. Buechter, Chester Springs, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/912,636

(22) Filed: Mar. 6, 2018

(65) Prior Publication Data
US 2018/0258453 A1 Sep. 13, 2018

Related U.S. Application Data

(60) Provisional application No. 62/467,917, filed on Mar. 7, 2017.

(51) Int. Cl.
| | | |
|---|---|---|
| C12P 19/04 | (2006.01) | |
| C12N 9/12 | (2006.01) | |
| C12N 1/20 | (2006.01) | |
| A61L 27/20 | (2006.01) | |
| C12N 9/10 | (2006.01) | |
| C12N 9/90 | (2006.01) | |
| C07K 14/245 | (2006.01) | |
| C12R 1/02 | (2006.01) | |

(52) U.S. Cl.
CPC .............. *C12P 19/04* (2013.01); *A61L 27/20* (2013.01); *C07K 14/245* (2013.01); *C12N 1/20* (2013.01); *C12N 9/1029* (2013.01); *C12N 9/1205* (2013.01); *C12N 9/90* (2013.01); *C12R 1/02* (2013.01); *C12Y 207/01059* (2013.01)

(58) Field of Classification Search
None
See application file for complete search history.

(56) References Cited

U.S. PATENT DOCUMENTS

| | | |
|---|---|---|
| 6,534,294 B1 | 3/2003 | Lee et al. |
| 7,332,304 B2 | 2/2008 | Deng et al. |
| 7,459,289 B2 | 12/2008 | Klaenhammer et al. |
| 7,510,725 B2 | 3/2009 | Damien et al. |
| 8,198,045 B2 | 6/2012 | Defrees et al. |
| 9,090,713 B2 | 7/2015 | Czaja et al. |
| 2002/0132320 A1 | 9/2002 | Wang et al. |
| 2004/0023361 A1 | 2/2004 | Gaier et al. |
| 2005/0042735 A1 | 2/2005 | Deng et al. |
| 2005/0239173 A1 | 10/2005 | McFarlan et al. |
| 2013/0122553 A1 | 5/2013 | Maertens et al. |
| 2016/0024543 A1 | 1/2016 | Merighi et al. |

FOREIGN PATENT DOCUMENTS

EP 1246922 B1 10/2010

OTHER PUBLICATIONS

Romling et al. Trends Microbiol. Sep. 2015; 23(9): 545-557. Published online Jun. 12, 2015 (Year: 2015).*
Tchieu et al. J Mol Microbiol Biotechnol. Jul. 2001;3(3):329-46. (Year: 2001).*
Olsen et al. Protein Sci. Jun. 2007; 16(6): 1230-1235 (Year: 2007).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Yadav et al: "Novel in vivo-degradable cellulose-chitin copolymer from metabolically engineered Gluconacetobacter xylinus" Applied and Environmental Microbiology, American Society for Microbiology, US, vol. 76, No. 18, Sep. 15, 2010 (Sep. 15, 2010), pp. 6257-6265.
Wendland et al, N-acetylglucosamine utilization by *Saccharomyces cerevisiae* based on expression of Candida albicans NAG genes, Applied and environmental microbiology, Sep. 15, 2009;75(18):5840-5845.
Ullah et al, Advances in biomedical and pharmaceutical applications of functional bacterial cellulose-based nanocomposites, Carbohydrate polymers, Oct. 5, 2016;150:330-352.
Silva et al, Bacterial cellulose surface modifications, Bacterial nanocellulose: a sophisticated multifunctional material, CRC Press, Boca Raton, 2013:91-111.
Postma et al, Phosphoenolpyruvate: carbohydrate phosphotransferase systems of bacteria, Microbiological reviews, Sep. 1, 1993;57(3):543-594.
Magdalena Oleksy et al: "Exopolysaccharides produced by *Lactobacillus* sp.: Biosynthesis and applications", Critical Reviews in Food Science and Nutrition, May 31, 2016 (May 31, 2016), pp. 1-13.
Madhuri et al: "Microbial Exopolysaccharides: Biosynthesis and Potential Applications", Oriental Journal of Chemistry, vol. 30, No. 3, Sep. 26, 2014 (Sep. 26, 2014), pp. 1401-1410.
Lustri et al, Microbial Cellulose—Biosynthesis Mechanisms and Medical Applications, Intech-Cellulose-Fundamental Aspects and Current Trends, 2015, pp. 133-157.
Lee et al, Direct Incorporation of Glucosamine and N-Acetylglucosamine into Exopolymers by Gluconacetobacter xylinus (= Acetobacter xylinum) ATCC 10245: Production of Chitosan-Cellulose and Chitin-Cellulose Exopolymers. Applied and environmental microbiology. Sep. 1, 2001,67(9):3970-3975.
Hossain et al, Metabolic engineering for amino-, oligo-, and polysugar production in microbes, Applied microbiology and biotechnology, Mar. 1, 2016;100(6):2523-2533.
Giavasis et al, Microbial Polysaccharides, 5-Functional food carbohydrates, 2006, pp. 167-213.

(Continued)

*Primary Examiner* — Christian L Fronda
(74) *Attorney, Agent, or Firm* — BakerHostetler

(57) ABSTRACT

The present disclosure is directed to microorganisms that are genetically modified to express at least one exogenous enzyme involved in N-acetylglucosamine uptake and metabolism. Methods for the production of an exopolysaccharide are also disclosed. The exopolysaccharide comprises N-acetylglucosamine and D-glucose and may be used as a bioresorbable implant for soft tissue repair, replacement, or augmentation.

2 Claims, No Drawings

(56) References Cited

OTHER PUBLICATIONS

Florea et al, Engineering control of bacterial cellulose production using a genetic toolkit and a new cellulose-producing strain. Proceedings of the National Academy of Sciences. Jun. 14, 2016;113(24):E3431-40.
De Vuyst L D et al: "Recent developments in the biosynthesis and applications of heteropolysaccharides from lactic acid bacteria", International Dairy Journal, Elsevier Applied Science, Barking, GB, vol. 11, No. 9, Jan. 1, 2001 (Jan. 1, 2001), pp. 687-707.
De Vos, Metabolic engineering of sugar catabolism in lactic acid bacteria, Antonie van Leeuwenhoek, Oct. 1, 1996;70(2-4):223-242.
Cheng, Production and application of bacterial cellulose, Current Topics in Biotechnology, vol. 5, 2009, 20 pages.
Chemical Abstracts Service No. 9027-48-9, STN: Nov. 16, 1984.
Chemical Abstracts Service No. 9027-51-4, STN: Nov. 16, 1984.
Chemical Abstracts Service No. 9023-06-7, STN: Nov. 16, 1984.
Christiansen et al, Staphylococcal phosphoenolpyruvate-dependent phosphotransferase system—two highly similar glucose permeases in *Staphylococcus carnosus* with different glucoside specificity: protein engineering in vivo?, Microbiology, Oct. 1, 1999;145(10):2881-2889.

\* cited by examiner

BACTERIUM FOR THE PRODUCTION OF AN EXOPOLYSACCHARIDE COMPRISING N-ACETYLGLUCOSAMINE AND D-GLUCOSE

CROSS REFERENCE TO RELATED APPLICATIONS

This application claims priority to U.S. Provisional Application No. 62/467,917 filed Mar. 7, 2017, the disclosure of which is hereby incorporated by reference in its entirety.

TECHNICAL FIELD

This disclosure relates to genetically-modified microorganisms and methods for the production of exopolysaccharides comprising N-acetylglucosamine and D-glucose monomers.

BACKGROUND

Cellulose produced in bacteria has several advantages compared to plant-derived cellulose for human health applications. Bacterial cellulose has high strength, excellent conformability and handling, good biocompatibility, and is free of lignins and other undesirable materials often found in plant cellulose. Because of these properties, bacterial cellulose is an attractive biomaterial for use in human health. In some human health applications, it is preferred that the material is bioresorbed as, for example, native human tissue is regenerated at the site where the bacterial cellulose has been placed. Because humans lack the enzymes capable of degrading cellulose, however, bacterial cellulose is not biodegradable in humans. Although various postproduction chemical processes have been developed to modify cellulose to make it susceptible to hydrolysis and hence, bioresorbable, these chemical processes can result in changes to the properties of the resulting material and loss of some of the desirable features of bacterial cellulose.

SUMMARY

Disclosed herein are microorganisms for the production of an exopolysaccharide wherein the microorganism expresses an exogenous enzyme. In one embodiment, the exogenous enzyme is N-acetylglucosamine phosphoenolpyruvate-dependent sugar phosphotransferase system permease or a biologically active homologue thereof. The microorganism produces an exopolysaccharide that comprises N-acetylglucosamine and D-glucose.

According to one embodiment, the microorganism further expresses at least one exogenous enzyme involved in N-acetylglucosamine uptake or metabolism. For example, the at least one exogenous enzyme involved in N-acetylglucosamine uptake or metabolism may comprise one or more of N-acetylglucosamine kinase, phosphoacetyl-glucosamine mutase, and UDP-N-acetylglucosamine pyrophosphorylase. Accordingly, in some embodiments, the microorganism further expresses at least one exogenous enzyme comprising one or more of N-acetylglucosamine kinase, phosphoacetyl-glucosamine mutase, and UDP-N-acetylglucosamine pyrophosphorylase. In preferred embodiments, the N-acetylglucosamine kinase and/or the UDP-N-acetylglucosamine pyrophosphorylase are derived from a source other than yeast.

Also provided herein are bacteria for the production of an exopolysaccharide wherein the bacteria expresses at least one exogenous enzyme, wherein the at least one exogenous enzyme is N-acetylglucosamine kinase, yeast-derived phosphoacetyl-glucosamine mutase, or UDP-N-acetylglucosamine pyrophosphorylase. The bacterium produces an exopolysaccharide that comprises N-acetylglucosamine and D-glucose. The N-acetylglucosamine kinase and the UDP-N-acetylglucosamine pyrophosphorylase may be derived from a source other than yeast, or the N-acetylglucosamine kinase may be derived from a source other than yeast and the UDP-N-acetylglucosamine pyrophosphorylase may be derived from yeast, or the N-acetylglucosamine kinase may be derived from yeast and the UDP-N-acetylglucosamine pyrophosphorylase may be derived from a source other than yeast.

In certain embodiments, the exogenous enzyme is encoded by a nucleic acid. In some embodiments, the nucleic acid can be a cDNA molecule. According to one embodiment, the nucleic acid is contained in a recombinant vector. For example, the recombinant vector may be a viral or a plasmid vector. According to a further embodiment, the nucleic acid is operably linked to a promoter. For example, the promoter may be a constitutive or inducible promoter.

Further disclosed are methods for producing exopolysaccharides that, according to one embodiment, comprises culturing a microorganism under conditions effective to produce the exopolysaccharide and recovering the exopolysaccharide. The microorganism expresses an exogenous enzyme, wherein the exogenous enzyme is N-acetylglucosamine phosphoenolpyruvate-dependent sugar phosphotransferase system permease or a biologically active homologue thereof. The microorganism produces an exopolysaccharide that comprises N-acetylglucosamine and D-glucose.

According to one embodiment, the microorganism further expresses at least one exogenous enzyme involved in N-acetylglucosamine uptake and/or metabolism. For example, the at least one exogenous enzyme involved in N-acetylglucosamine uptake or metabolism may comprise one or more of N-acetylglucosamine kinase, phosphoacetyl-glucosamine mutase, and UDP-N-acetylglucosamine pyrophosphorylase. According, in some embodiments, the microorganism further expresses at least one exogenous enzyme comprising one or more of N-acetylglucosamine kinase, phosphoacetyl-glucosamine mutase, or UDP-N-acetylglucosamine pyrophosphorylase. In some aspects, the N-acetylglucosamine kinase and/or the UDP-N-acetylglucosamine pyrophosphorylase are derived from a source other than yeast.

Methods for producing an exopolysaccharide are also provided, wherein the methods comprise culturing a microorganism under conditions effective to produce the exopolysaccharide and recovering the exopolysaccharide. The microorganism expresses at least one exogenous enzyme, wherein the at least one exogenous enzyme is N-acetylglucosamine kinase, yeast-derived phosphoacetyl-glucosamine mutase, or UDP-N-acetylglucosamine pyrophosphorylase, wherein the exopolysaccharide comprises N-acetylglucosamine and D-glucose. The N-acetylglucosamine kinase and the UDP-N-acetylglucosamine pyrophosphorylase may be derived from a source other than yeast, or the N-acetylglucosamine kinase may be derived from a source other than yeast and the UDP-N-acetylglucosamine pyrophosphorylase may be derived from yeast, or the N-acetylglucosamine kinase may be derived from yeast and the UDP-N-acetylglucosamine pyrophosphorylase may be derived from a source other than yeast.

The microorganism described herein may be a bacterium. In some embodiments, the bacterium belongs to the family Acetobacteraceae. Exemplary bacterium from the family Acetobacteraceae include those of the genus *Komagataeibacter* and *Gluconacetobacter*. In some embodiments, the bacterium belongs to a genus comprising *Agrobacterium, Aerobacter, Achromobacter, Azotobacter, Rhizobium, Sarcina,* or *Salmonella*. In preferred embodiments, the bacterium is *Komagataeibacter xylinus*.

The microorganism may be cultured in a culture medium containing D-glucose, N-acetylglucosamine, glucosamine, 3-O-methylglucose, 2-deoxyglucose, or a combination thereof.

Also described herein are methods of treating the exopolysaccharide after it is produced by the microorganism. In some embodiments, the exopolysaccharide may be at least partially dehydrated by, for example, mechanical pressing and/or critical point drying using supercritical carbon dioxide. In some embodiments, the exopolysaccharide may be contacted with one or more active agents. In some embodiments, the exopolysaccharide may be further reacted with an oxidizing agent so as to form a body of oxidized exopolysaccharide. For example, the oxidizing agent may comprise metaperiodate, hypochlorite, dichromate, peroxide, permanganate, or nitrogen dioxide. In some embodiments, the oxidizing agent is sodium metaperiodate.

The present disclosure further describes implants for soft tissue repair, replacement, or augmentation comprising the exopolysaccharide produced by any of the methods described herein. In preferred embodiments, the implant is used in hernia repair, repair of dura mater, replacement of dura mater, or any combination thereof.

DETAILED DESCRIPTION

It is to be understood that the disclosed microorganisms and methods are not limited to the specific microorganisms and methods described and/or shown herein, and that the terminology used herein is for the purpose of describing particular embodiments by way of example only and is not intended to be limiting of the claimed microorganisms and methods.

Unless specifically stated otherwise, any description as to a possible mechanism or mode of action or reason for improvement is meant to be illustrative only, and the disclosed microorganisms and methods are not to be constrained by the correctness or incorrectness of any such suggested mechanism or mode of action or reason for improvement.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed microorganisms and methods which are, for clarity, described herein in the context of separate embodiments, may also be provided in combination in a single embodiment. Conversely, various features of the disclosed microorganisms and methods that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

The term "comprising" is intended to include examples encompassed by the terms "consisting essentially of" and "consisting of"; similarly, the term "consisting essentially of" is intended to include examples encompassed by the term "consisting of."

The term "exogenous" refers to any protein that does not originate from that particular cell as found in nature. Accordingly, non-naturally-occurring proteins are considered to be exogenous to a cell once introduced into the cell.

Because bacterial cellulose is not biodegradable in humans, there exists a need to produce a bioresorbable exopolysaccharide that exhibits the desired features of bacterial cellulose. One approach to generate such a bioresorbable exopolysaccharide is to modify a bacterium that produces cellulose such that chemical linkages that are susceptible to cleavage by human enzymes are incorporated into the exopolysaccharide during production. Bacterial cellulose is a polysaccharide comprised of $\beta(1\text{-}4)$-linked D-glucose monomers. These units can be cleaved by cellulase enzymes; however, these enzymes are not present in humans and consequently bacterial cellulose is not biodegradable in humans. N-acetylglucosamine (GlcNac) is a naturally occurring monosaccharide. Polysaccharides comprised of $\beta(1\text{-}4)$-linked GlcNac residues, such as chitin, are substrates for human lysozyme enzymes and consequently are biodegradable in humans. Incorporation of $\beta(1\text{-}4)$-linked GlcNac residues instead of $\beta(1\text{-}4)$-linked D-glucose into an exopolysaccharide produced in bacteria results in an exopolysaccharide where some number of the glucose units are replaced by GlcNac units, and is susceptible to human lysozyme and therefore bioresorbable in humans.

Efficient incorporation of GlcNac residues into a bacterial exopolysaccharide can depend on the appropriate amount of GlcNac monomers in an appropriate chemical form present intracellularly in the producing bacteria so that the GlcNac monomers will be utilized as a substrate by the bacterial cellulose biosynthetic machinery. Utilization by the cellulose biosynthesis machinery of the GlcNac substrate in competition with the natural glucose substrate results in a heterogeneous exopolysaccharide where biodegradable chemical linkages are substituted for a portion of the β(1-4) glucose linkages. For cellulose production in *Komagataeibacter xylinus* (*K. xylinus*), for example, the uridine diphosphate monosaccharide form of the monomer (either UDP-glucose or UDP-GlcNac) is utilized as substrate for the cellulose synthase enzyme. In turn, UDP-GlcNac is produced from the reaction of GlcNac-1-phosphate and UTP catalyzed by a UDP-GlcNac-pyrophosphorylase. GlcNac-1-phosphate is made by isomerization of GlcNac-6-phosphate catalyzed by phosphoacetyl-glucosamine mutase.

The sequence outlined above starts with the efficient accumulation of GlcNac-6-phosphate intracellularly in the bacterium. Bacterial phosphoenolpyruvate:GlcNac phosphotransferase systems mediate the transport of GlcNac intracellularly from the extracellular milieu, which also results in the simultaneous phosphorylation of GlcNac at the 6 position to form GlcNac-6-phosphate. Thus, genetically modifying *K. xylinus* to overexpress a GlcNac phosphotransferase results in both the efficient transport of GlcNac into the cell and its conversion to the 6 phosphate form that is the starting point for ultimate incorporation into a cellulose-based polysaccharide. Genetically engineered microorganisms, including bacteria, and methods of producing exopolysaccharides are provided herein.

Microorganisms for the Production of Exopolysaccharides

Provided herein are microorganisms for the production of exopolysaccharides wherein the microorganisms express an exogenous enzyme. Suitable microorganisms include, but are not limited to, bacteria and fungi. In one embodiment, the fungi can be a yeast including, but not limited to, a yeast of the genus *Saccharomyces*, *Candida*, *Hansenula*, *Pichia*, *Kluveromyces*, *Phaffia*, and *Schizosaccharomyces*. Suitable yeast include, but are not limited to, yeast from the species selected from *Saccharomyces cerevisiae*, *Schizosaccharomyces pombe*, *Candida albicans*, *Hansenula polymorpha*, *Pichia pastoris*, *P. canadensis*, *Kluyveromyces marxianus* and *Phaffia rhodozyma*. In another embodiment, the microorganism can be a fungus including, but not limited to, a fungus of the genus *Aspergillus*, *Absidia*, *Rhizopus*, *Chrysosporium*, *Neurospora* and *Trichoderma*. Suitable fungi include, but are not limited to, fungi from the species selected from *Aspergillus niger*, *A. nidulans*, *Absidia coerulea*, *Rhizopus oryzae*, *Chrysosporium lucknowense*, *Neurospora crassa*, *Nintermedia* and *Trichoderm reesi*. In a further embodiment, the microorganism can be a bacterium. In some embodiments, the bacterium belongs to the family Acetobacteraceae, including those of the genus *Komagataeibacter* and *Gluconacetobacter*. In some embodiments, the bacterium belongs to the genus *Escherichia*, *Bacillus*, *Lactobacillus*, *Pseudomonas*, *Streptomyces*, *Agrobacterium*, *Aerobacter*, *Achromobacter*, *Azotobacter*, *Rhizobium*, *Sarcina*, or *Salmonella*. Preferably, the bacteria belong to the genus *Komagataeibacter*, *Gluconacetobacter*, *Agrobacterium*, *Aerobacter*, *Achromobacter*, *Azotobacter*, *Rhizobium*, *Sarcina*, or *Salmonella*. Suitable bacteria include, but are not limited to, bacteria from the species selected from *Escherichia coli*, *Bacillus subtilis*, *Bacillus licheniformis*, *Lactobacillus brevis*, *Pseudomonas aeruginosa*, *Streptomyces lividans*, *Gluconacetobacter xylinus* and *Komagataeibacter xylinus*. Most preferably, the bacterium belongs to the species *Komagataeibacter xylinus*.

The microorganism produces an exopolysaccharide that comprises N-acetylglucosamine and D-glucose. As used herein, "exopolysaccharide" refers to a polymer of glucose and glucose analog residues secreted by a microorganism such as a bacterium. In some aspects, the exopolysaccharide may be microbial cellulose ((1-4)-linked-β-D-glucan), which is composed of monomers bound by β(1-4) linkages with the chemical formula $(C_6H_{10}O_5)_n$. Glucose, also referred to as D-Glucose, (2R,3S,4R,5R)-2,3,4,5,6-Pentahydroxyhexanal or Glc, has the chemical formula $C_6H_{12}O_6$ and the Chemical Abstracts Service registry number 50-99-7. According to another aspect, the exopolysaccharide may be chitin ((1-4)-linked 2 acetoamino-2-deoxy-β-D-glucose), which is composed of N-acetylglucosamine monomers bound by β(1-4) linkages with the chemical formula $(C_8H_{13}O_5N)_n$. Chitin may also exist as a copolymer of N-acetylglucosamine and N-glucosamine residues. N-acetylglucosamine, also referred to as β-D-(Acetylamino)-2-deoxy-glucopyranose, N-acetyl-D-glucosamine, GlcNAC, or NAG, has the chemical formula $(C_6H_{15}NO_6)$ and the Chemical Abstracts Service registry number 7512-17-6. In preferred embodiments, the exopolysaccharide may be a copolymer, meaning a polymer composed of at least two different monomer subunits. In most preferred embodiments, the exopolysaccharide comprises cellulose-chitin (glucose:N-acetylglucosamine) copolymers. A mixture of different molar ratios of glucose to N-acetylglucosamine may be synthesized by the disclosed methods.

In one embodiment, the microorganism expresses the exogenous enzyme N-acetylglucosamine phosphoenolpyruvate-dependent sugar phosphotransferase system permease or a biologically active homologue thereof. N-acetylglucosamine phosphoenolpyruvate-dependent sugar phosphotransferase system permease ($EII^{Nag}$) is a type II enzyme encoded by the gene nagE, which has been sequenced in *E. coli* (EcoGene EG10635) and *K. pneumoniaei* (GenBank X63289). $EII^{Nag}$ is a component of the phosphoenolpyruvate (PEP):carbohydrate phosphotransferase system (PTS), which is involved in the transport and phosphorylation of a large number of carbohydrates. In particular, $EII^{Nag}$ is a multidomain, membrane-spanning protein responsible for the phosphorylation of N-acetylglucosamine at the 6 position to form N-acetylglucosamine-6-phosphate while the N-acetylglucosamine is being transported across the inner membrane. $EII^{Nag}$ may also be referred to as N-acetylglucosamine PTS permease, $II^{Nag}$, pLC5-21, GlcNAc-specific enzyme II, or IIN-acetylglucosamine. Expression or overexpression of the $EII^{Nag}$ protein will result in the production of an exopolysaccharide that comprises N-acetylglucosamine and D-glucose monomers.

As used herein, the term "express" refers to the process by which information from a gene is first converted into messenger RNA (transcription) and then to a functional gene product such as proteins (translation) as well as non-protein coding genes such as transfer RNA or small nuclear RNA. "Overexpression" refers to an increased frequency of expression relative to endogenous levels.

The microorganism can further express at least one exogenous enzyme involved in N-acetylglucosamine uptake or metabolism. The at least one exogenous enzyme involved in N-acetylglucosamine uptake or metabolism may comprise one or more of N-acetylglucosamine kinase, phosphoacetylglucosamine mutase, or UDP-N-acetylglucosamine pyrophosphorylase. Accordingly, in some embodiments, the microorganism can further express at least one exogenous enzyme comprising one or more of N-acetylglucosamine kinase, phosphoacetyl-glucosamine mutase, or UDP-N-acetylglucosamine pyrophosphorylase. In other preferred embodiments, the N-acetylglucosamine kinase and/or the UDP-N-acetylglucosamine pyrophosphorylase are derived from a source other than yeast.

In some embodiments, the exogenous enzyme can be encoded by a nucleic acid. Suitable nucleic acids include, for example, cDNA molecules. In some aspects, the nucleic acid is contained in a recombinant vector. The recombinant vector can be a viral or a plasmid vector. The nucleic acid can be operably linked to a promoter, such as a constitutive or inducible promoter.

Provided herein are bacteria for the production of an exopolysaccharide wherein the bacteria expresses at least one exogenous enzyme, wherein the at least one exogenous enzyme is N-acetylglucosamine kinase, yeast-derived phosphoacetyl-glucosamine mutase, or UDP-N-acetylglucosamine pyrophosphorylase. The bacteria produce an exopolysaccharide that comprises N-acetylglucosamine and D-glucose. The N-acetylglucosamine kinase and the UDP-N-acetylglucosamine pyrophosphorylase may be derived from a source other than yeast, or the N-acetylglucosamine kinase may be derived from a source other than yeast and the UDP-N-acetylglucosamine pyrophosphorylase may be derived from yeast, or the N-acetylglucosamine kinase may be derived from yeast and the UDP-N-acetylglucosamine pyrophosphorylase may be derived from a source other than yeast.

N-acetylglucosamine kinase (Chemical Abstracts Service Number 9027-48-9) is an enzyme that catalyzes the conversion of N-acetylglucosamine to N-acetylglucosamine-6-phosphate. N-acetylglucosamine kinase, also referred to as GlcNAc kinase, N-acetylglucosamine kinase, NAG5, NAGK, and N-acetyl-D-glucosamine-6-phosphotransferase, belongs to a family of transferases implicated in the transfer of phosphorous-containing groups to an alcohol acceptor. Accordingly, N-acetylglucosamine kinase works in parallel with EII$^{Nag}$ to generate N-acetylglucosamine-6-phosphate, which may be used as a substrate for further downstream enzymatic reactions.

Phosphoacetyl-glucosamine mutase (Chemical Abstracts Service Number 9027-51-4) is an enzyme that belongs to the phosphohexose mutase family, which catalyzes the conversion of N-acetylglucosamine-6-phosphate to N-acetylglucosamine-1-phosphate. Phosphoacetyl-glucosamine mutase is also known as N-acetyl-alpha-D-glucosamine 1,6-phosphomutase, acetylglucosamine phosphomutase, acetylglucosamine phosphomutase, acetylaminodeoxyglucose phosphomutase, phospho-N-acetylglucosamine mutase, AGM1, PCM1, PGM3, and N-acetyl-D-glucosamine 1,6-phosphomutase. In preferred embodiments, phosphoacetyl-glucosamine mutase is derived from yeast such as, for example, the species *C. albicans* or *S. cerevisiae*. The *C. albicans* phosphoacetyl-glucosamine mutase is encoded by the agm1 gene. The *S. cerevisiae* the phosphoacetyl-glucosamine mutase is encoded by the pcm1 gene.

UDP-N-acetylglucosamine pyrophosphorylase (Chemical Abstracts Service Number 9023-06-7) catalyzes the conversion of N-acetylglucosamine-1-phosphate to UDP-N-acetylglucosamine. UDP-N-acetylglucosamine pyrophosphorylase is also referred to as UTP:N-acetyl-alpha-D-glucosamine-1-phosphate uridylyltransferase, UDP-GlcNAc pyrophosphorylase, UAP1, and acetylglucosamine 1-phosphate uridylyltransferase. UDP-N-acetylglucosamine pyrophosphorylase is a member of the family of nucleotide diphosphate sugar pyrophosphorylases, comprising a subfamily of UDP-sugar pyrophosphorylases. In *Escherichia coli*, the glmU gene encodes for a bifunctional UDP-N-acetylglucosamine pyrophosphorylase/Glucosamine-1-phosphate N-acetyltransferase (EC:2.7.7.23 and 2.3.1.157) enzyme that catalyzes the last two sequential reactions in the de novo biosynthetic pathway for UDP-N-acetylglucosamine (UDP-GlcNAc): 1) the C-terminal domain catalyzes the transfer of an acetyl group from acetyl coenzyme A to glucosamine-1-phosphate (GlcN-1-P) to produce N-acetylglucosamine-1-phosphate (GlcNAc-1-P); and 2) the N-terminal domain catalyzes the transfer of a uridine 5-monophosphate (from uridine 5-triphosphate) to the N-acetylglucosamine-1-phosphate to form UDP-GlcNAc. In some embodiments, the UDP-N-acetylglucosamine pyrophosphorylase is encoded by the *Escherichia coli* glmU gene.

In certain embodiments, the exogenous enzyme is encoded by a nucleic acid. The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogs of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (e.g., phosphorothioates, phosphoroamidates). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions are achieved by generating sequences in which the third position of one or more selected (or all) codons is substituted with mixed-base and/or deoxyinosine residues.

In some embodiments, the nucleic acid is a cDNA molecule.

The nucleic acids can be contained in a recombinant vector such as, for example, plasmids, phage, phagemids, viruses, artificial chromosomes and the like. In some embodiments, the recombinant vector is a viral or plasmid vector. Preferably, the vector is capable of replicating autonomously within the microorganism. Alternatively, the vector may integrate into the host's genome. More preferably, the vector is an expression vector. The nucleic acid may be operably linked to a promoter. More than one gene may be operably linked to a single promoter. The term "operably linked" means a functional linkage between a nucleic acid expression control sequence such as a promoter and a second nucleic acid sequence, wherein the expression control sequence affects transcription and/or translation of the nucleic acid corresponding to the second sequence. In some embodiments, the promoter is a constitutive or inducible promoter.

The coding region of the gene may be altered prior to insertion into or within the recombinant vector such as by deletion, addition or substitution. In certain embodiments, it may be desirable to alter the function or specificity of the enzyme. Additionally, the coding regions of two or more enzymes may be linked to create a fusion protein.

The bacterium can belong to the family Acetobacteraceae or a genus comprising *Komagataeibacter, Gluconacetobacter, Agrobacterium, Aerobacter, Achromobacter, Azotobacter, Rhizobium, Sarcina*, and *Salmonella*. In some embodiments, the bacterium is *Komagataeibacter xylinus*.

Methods of Producing Exopolysaccharides

The present disclosure additionally describes methods for producing exopolysaccharides comprising culturing a microorganism under conditions effective to produce the exopolysaccharide and recovering the exopolysaccharide. The microorganism expresses an exogenous enzyme, wherein the exogenous enzyme can be N-acetylglucosamine phosphoenolpyruvate-dependent sugar phosphotransferase system permease or a biologically active homologue thereof. The exopolysaccharide comprises N-acetylglucosamine and D-glucose.

The microorganism can further express at least one exogenous enzyme involved in N-acetylglucosamine uptake and metabolism. The at least one exogenous enzyme involved in N-acetylglucosamine uptake and metabolism can comprise one or more of N-acetylglucosamine kinase, phosphoacetylglucosamine mutase, or UDP-N-acetylglucosamine pyrophosphorylase. In some aspects, the N-acetylglucosamine kinase and/or the UDP-N-acetylglucosamine pyrophosphorylase are derived from a source other than yeast.

In some aspects of the disclosed methods, the microorganism is a bacterium. Thus, the methods for producing an exopolysaccharide can comprise culturing a bacterium under conditions effective to produce the exopolysaccharide, and recovering the exopolysaccharide.

Exemplary bacterium are those belonging to a genus comprising *Komagataeibacter, Gluconacetobacter, Agrobacterium, Aerobacter, Achromobacter, Azotobacter, Rhizobium, Sarcina*, and *Salmonella*. In some embodiments, for example, the bacterium can be *Komagataeibacter xylinus*.

In embodiments wherein the microorganism is a bacterium, the at least one exogenous enzyme can be N-acetylglucosamine kinase, yeast-derived phosphoacetyl-glucosamine mutase, or UDP-N-acetylglucosamine pyrophosphorylase. The N-acetylglucosamine kinase and the UDP-N-acetylglucosamine pyrophosphorylase are derived from a source other than yeast, or the N-acetylglucosamine kinase is derived from a source other than yeast and the UDP-N-acetylglucosamine pyrophosphorylase is derived from yeast, or the N-acetylglucosamine kinase is derived yeast and the UDP-N-acetylglucosamine pyrophosphorylase is derived from a source other than yeast.

In the above disclosed methods for producing an exopolysaccharide, the microorganism (including the bacterium) can be cultured in a culture medium containing D-glucose, N-acetylglucosamine, glucosamine, 3-O-methylglucose, 2-deoxyglucose, or a combination thereof.

In preparing the exopolysaccharides, microorganisms such as *Komagataeibacter xylinus* (*Acetobacter xylinum*) expressing one or more exogenous enzymes as presently described are cultured (incubated) in a bioreactor containing a liquid nutrient medium at about 30° C. at an initial pH of about 4.1 to about 4.5. Exopolysaccharide production can be achieved using, for example, sucrose, glucose, N-acetylglucosamine, glucosamine, 3-O-methylglucose, and/or 2-deoxyglucose as a carbon source, ammonium salts as a nitrogen source, and corn steep liquor as nutrient source.

Suitable bioreactors are selected which minimize evaporation and provide adequate oxygen-limiting conditions. The bioreactor may be composed of a clean, dry plastic box fitted with an airtight or limited gas-permeable cover. An aeration port can be added to regulate the oxygen-limiting conditions. Dimensions of the bioreactor can vary in configuration depending on the desired shape, size, thickness, and yield of the exopolysaccharide being produced. Such systems are able to provide oxygen-limiting conditions that help ensure formation of a uniform exopolysaccharide membrane.

The main fermentation process, following the incubation step, is typically carried out under stationary conditions for a period of about 8-120 hours, preferably 24-72 hours, during which the bacteria in the culture medium synthesize and deposit thin layers of exopolysaccharide sheets, thus forming an exopolysaccharide membrane (pellicle). Depending on the desired thickness and/or exopolysaccharide yield, the fermentation can be stopped, at which point the membrane can be harvested from the bioreactor. According to one embodiment, the main fermentation is stopped after a relatively short period to yield a uniform, low exopolysaccharide content membrane. The excess medium contained in the pellicle is then removed by standard separation techniques such as compression or centrifugation, which results in a partially dehydrated pellicle.

The partially dehydrated exopolysaccharide pellicle can then be subjected to a purification processing that renders the exopolysaccharide nonpyrogenic. According to one embodiment, the purification method is a chemical purification of the exopolysaccharide membrane. The exopolysaccharide can be subjected to a series of caustic (e.g., concentrated sodium hydroxide) chemical wash steps to convert the exopolysaccharide membrane into a nonpyrogenic material, followed by soaking and/or rinsing with filtered water, until a neutral pH is achieved. Alternatively, or in conjunction with these steps, a short soak in diluted acetic acid can also be conducted to ensure neutralization of the remaining sodium hydroxide. Purification processes using various exposure times, concentrations and temperatures, as well as mechanical techniques including pressing, can be utilized on either the purified or unpurified exopolysaccharide membrane. Processing times in sodium hydroxide of about 1 hour to about 12 hours have been studied in conjunction with temperature variations of about 30° C. to about 100° C. to optimize the process. A preferred or recommended temperature processing occurs at or near 70° C.

The amount of endotoxins left in the exopolysaccharide after processing may be measured by Limulus Amebocyte Lysate (LAL) test. The cleaning process described herein is capable of providing a nonpyrogenic exopolysaccharide membrane (<0.06 EU/ml). Following the purification of the exopolysaccharide membrane, according to one embodiment, the pellicle can be mechanically compressed to a desired weight and thickness.

The exopolysaccharide membrane can undergo critical point drying. Critical point drying is a stepwise process wherein water in the exopolysaccharide membrane is exchanged with a non-aqueous solvent that is soluble with water, for example ethanol. The ethanol is then displaced with liquid carbon dioxide. This drying process can enhance the penetration of the oxidizing agent into the exopolysaccharide membrane. The dried membrane can be further reacted with an oxidizing agent, as described below, and recovered and washed in a manner as described above.

In another embodiment, the exopolysaccharide may be at least partially dehydrated by, for example, mechanical pressing. Following the purification and/or oxidations steps described above, the exopolysaccharide pellicle is mechanically compressed to the predetermined weight desired for form, fit, and function for soft tissue repair, replacement, or augmentation, e.g., hernia repair. The original fill volume and the compression steps are integral to attain the desired density that affects the strength, integrity, and function of the exopolysaccharide. Partially dehydrated samples are packaged in a single- or double-pouch system in preparation for sterilization. Samples are tested for exopolysaccharide content, endotoxin, and mechanical strength.

Further processing may continue with placing the exopolysaccharide in a closed container and decreasing the temperature to below 0° C. After a period of time, the temperature is increased to above freezing and excess moisture that is released from the exopolysaccharide is removed. This results in partially dehydrated exopolysaccharide. Without being bound to any one theory, it is believed that at below 0° C., water crystals form and are brought to the surface of the exopolysaccharide mesh. At above freezing temperature the liquid that has been removed is not allowed to rehydrate the surgical mesh, thereby yielding a product having increased tensile strength, elongation (stretch), conformability, and suture retention when used as an implantable medical device for various surgical procedures. Depending on the desired level of dehydration, the films are exposed to one or more temperature variation cycles. The excess liquid is removed by pouring, dabbing, or vacuuming it off. The partially dehydrated material is packaged in a single- or double-pouch system in preparation for sterilization. Samples are tested for exopolysaccharide content, endotoxin (LAL), and mechanical strength.

The exopolysaccharide may be at least partially dehydrated by critical point drying using supercritical carbon dioxide. Thus, in some embodiments, the disclosed methods can further comprise the step of at least partially dehydrating the body of the exopolysaccharide by critical point drying using supercritical carbon dioxide. As previously explained above, the water in the exopolysaccharide membrane is exchanged with a non-aqueous solvent (e.g., ethanol). The solvent is then replaced with liquid carbon dioxide through a process called critical point drying. During critical point drying, the exopolysaccharide membranes are loaded onto a holder, sandwiched between stainless steel mesh plates, and then soaked in a chamber containing supercritical carbon dioxide under pressure. The holder is designed to allow the $CO_2$ to circulate through the exopolysaccharide membrane while mesh plates stabilize the membrane to prevent the membrane from waving during the drying process. Once all of the organic solvent has been removed (which in most typical cases is in the range of about 1-6 hours), the liquid $CO_2$ temperature is increased above the critical temperature for carbon dioxide so that the $CO_2$ forms a supercritical fluid/gas. Due to the fact that no surface tension exists during such transition, the resulting product is a dried membrane which maintains its shape, thickness, and 3-D nanostructure. The dried product undergoes cutting, packaging, and sterilization.

The exopolysaccharides produced from the disclosed methods can be further contacted with one or more active agents. Suitable active agents include any compositions suitable for treatment at an anatomical location, such as, bone marrow, autograft, osteoinductive small molecules, osteogenic material, stem cells, bone morphogenetic proteins, antibacterial agents, calcium phosphate ceramics, and mixtures and blends thereof.

The exopolysaccharide can be reacted with an oxidizing agent. Suitable oxidizing agents include, for example, metaperiodate, hypochlorite, dichromate, peroxide, permanganate, or nitrogen dioxide. In some embodiments, the oxidizing agent is sodium metaperiodate. The oxidizing agent can have, according to one embodiment, a concentration range of about 0.01M to about 10.0M, preferably about 0.05M to about 1.0M, and more preferably from about 0.1M to about 0.5M. It should be noted that when selecting metaperiodate, the reaction is preferably conducted in the dark. According to one embodiment, the oxidation reaction with the oxidizing agent is for a time period in the range of about 30 minutes to 72 hours, preferably about 2-16 hours, and more preferably about 2-6 hours. The oxidation reaction can typically proceed at a temperature range of 18° C. to 60° C., preferably 30° C. to 50° C., and more preferably at about 40° C. According to another embodiment, the oxidation reaction with the oxidizing agent is for a time period of at least about one hour, and in yet another embodiment for at least about 3 hours. The container(s) are placed on a shaker and agitated at 20-500 rpm, preferably 350-450 rpm. The molar ratio between exopolysaccharide and metaperiodate can be maintained at the range of 1:1-1:160, preferably 1:1-1:120, and more preferably at about 1:120. Upon completion of the oxidation reaction, the oxidized exopolysaccharide membrane can be washed multiple times in filtered water on an ice-bath to remove excess metaperiodate. Alternatively, it can be washed in ethylene glycol to neutralize metaperiodate followed by multiple rinses in DI water.

The oxidized exopolysaccharide can have a variable range of degree of oxidation, which can, according to one embodiment, be in the range of about 0 percent to about 99 percent oxidation, for example in a range of about 20 percent to about 70 percent. The degree of oxidation of the irradiated oxidized exopolysaccharide can depend on the oxidizing agent selected, the concentration range of the oxidizing agent, reaction temperature, and the time period of the reaction between the irradiated exopolysaccharide and the oxidizing agent. According to one embodiment, the degree of oxidation is in the range of about 15 percent to about 80 percent, and in another embodiment is in the range of about 20 percent to about 70 percent. In addition, the exopolysaccharide membrane can be ground up to form a slurry and then homogenized into a fine suspension of fibers. The suspension can then be placed in a mold and cross-linked to form a stable exopolysaccharide membrane again.

Oxidation may be performed after the exopolysaccharide undergoes critical point drying, partial dehydration, and/or contact with one or more active agents.

Exopolysaccharide Implants

Also provided are exopolysaccharide products produced by the processes disclosed herein. In particular, the present disclosure further describes implants for soft tissue repair, replacement, or augmentation comprising the exopolysaccharide produced by any of the methods described herein. The implant can be used in hernia repair, repair of dura mater, replacement of dura mater, or any combination thereof. According to the present disclosure, an implant is described having sufficient mechanical strength, conformability to anatomical surfaces, and resorption profile for use in tissue repair, replacement, and/or augmentation procedures, particularly soft tissue applications.

In certain medical procedures, it is desirable to have additional medical devices present at the anatomical location in order to provide additional support, fixation, and/or stabilization at the locus of repair, replacement, and/or augmentation. Where such secondary medical devices are desired, the implant surface in the hydrated state can be conformable to the anatomical surface, the secondary medical device surface, and/or both surfaces. Examples of suitable secondary medical devices can include, but are not limited to, bone screws, bone plates, metallic and polymer meshes, as well as metallic and polymer plates and caps such as those used in cranial surgeries.

The implant may have a variable range of degradation profiles that can be manipulated to align with the clinical indication for which it is intended to be implanted. For example, when the implant is selected for use in hernia repair, the porous body that forms the implant can have a degradation profile that substantially matches the natural tissue replacement rate of native dura mater. In vitro degradation testing, done under conditions simulating an in vivo environment, can be performed to evaluate an implant's degradation profile with respect to a desired clinical indication. In vitro testing can be conducted for any length of time as is desired, for example, one day, one week, four weeks, two months, six months, one year, or multiple years. According to one embodiment, the porous body has a one week in vitro degradation profile (as explained in further detail below) under simulated body fluid (SBF) conditions in the range of about zero to about 90 percent.

According to a further embodiment, the exopolysaccharide can be a scaffold or carrier for one or more active agents. The active agent or agents can be impregnated within the porous body of exopolysaccharide that forms the implant, coated onto a surface of the implant, and/or both. According to one embodiment, the active agent or agents can be impregnated within and/or coated onto the implant substantially at or near the time of implantation (i.e., intraoperatively). In an alternative embodiment, the active agent or agents can be impregnated within and/or coated onto the implant prior to the time of implantation (i.e., preoperatively). In certain embodiments, more than one active agent can be impregnated within and/or coated onto the implant, and further the more than one active agents can be impregnated within and/or coated onto the implant at different time periods. For example, some active agents can be preoperatively combined with the implant, while other active agents can be combined intraoperatively. Active agents that can be utilized with the implant include any compositions suitable for treatment at the anatomical location, such as, bone marrow, autograft, osteoinductive small molecules, osteogenic material, stem cells, bone morphogenetic proteins, antibacterial agents, calcium phosphate ceramics, and mixtures and blends thereof.

EXAMPLES

The following examples are provided to further describe some of the embodiments disclosed herein. The examples are intended to illustrate, not to limit, the disclosed embodiments.

Example 1: Microorganism and Culture Conditions

A proprietary *Komagataeibacter xylinus* strain from the collection of Synthes, Inc., which has the ability to yield pellicles of above normal thicknesses for most stains of *Komagataeibacter xylinus*, is used in this study. Other strains of *K. xylinus*, or other bacteria, including those of the genera *Gluconacetobacter, Komagataeibacter, Sarcina*, and *Agrobacterium*, can also be used. Culture media is based on various sugars including monosaccharides (such as glucose, fructose, galactose, xylose), disaccharides (such as sucrose, maltose, lactose), sugar alcohols (such as glycerol or arabitol), or combinations thereof. Nitrogen sources in the medium are also important for pellicle uniformity and growth as well as pellicle hue. Corn steep liquor serves as the nitrogen source in the subject medium. Other sources include bacterial, vegetable, or animal peptones, waste beer yeast, cabbage juice, and dry oil mill residues. Various salts and amino acids are added to the medium to promote propagation and cellular metabolism. The homogenous medium is sterilized to mitigate contamination risk and to promote the hydrolysis of disaccharides into monosaccharides. The extent of hydrolysis is dependent on heat energy transferred during the sterilization process. Steam lethality serves as a potential measure of heat energy. Desirable lethality ranges from 6 to 40 minutes, measured directly with a thermocouple, which is essential in determining accurate lethality values.

The cells for the inoculum are cultured in Erlenmeyer flasks filled with media for a period of 1-3 days at 30±2° C. The inoculated media with deposited pellicle is then gently stirred and used as inoculum to conduct large-scale fermentation in tray reactors. The trays are incubated in static conditions at 30±2° C. for a period of 5-60 days until a uniform pellicle with the appropriate thickness is formed on the surface. Pellicles are harvested and purified by washing with 1-6% aqueous NaOH with 1-4 cycles for 1-5 hrs total time. Pellicles are bleached with 0.1-1% $H_2O_2$ for 1-2 cycles for 1-2 hrs total time followed by soaking in multiple changes of distilled water until neutral pH is reached. Finally, the pellicles are mechanically pressed to the desired thicknesses. Pellicles are processed through either thermal modification via freezing and dehydration at −5° C. to −80° C. for 1-30 days or chemical treatment using, for example, acetone, methanol, ethanol, or other water miscible organic solvents. Pellicles may be γ-irradiated at the range of 22.5-29 kGy or steam-sterilized. Additional water may be extracted by treatment with ethanol or methanol. Pellicles may be processed through a critical point drying system prior to proceeding to sterilization steps.

Example 2: Cloning and Expression of *Escherichia Coli* Derived N-Acetylglucosamine Phosphoenolpyruvate-Dependent Sugar Phosphotransferase System Permease in *Komagataeibacter xylinus* and the Production of an Exopolysaccharide Containing D-Glucose and N-Acetylglucosamine The *Escherichia coli* nagE gene (encoding N-acetylglucosamine phosphoenolpyruvate-dependent sugar phosphotransferase system permease, EC 2.7.1.193) is cloned into the expression vector pSEVA331 (GenBank: JX560333.1) under control of the LuxR promoter (Florea, et al 2016a). *K. xylinus* is transformed with the resulting plasmid as described by Florea, et al, 2016a and 2016b. Transformed bacteria are cultured in Erlenmeyer flasks filled with media for a period of 1-3 days at 30±2° C. as described in Example 1, above. The inoculated media with deposited pellicle is gently stirred and used as inoculum to conduct a larger-scale fermentation in tray reactors as described in Example 1, above, except the media in the tray reactors is further supplemented with 0.5-2% N-acetylglucosamine and 0.01-1 µM N-acyl homoserine lactone.

Pellicles of exopolysaccharide comprising D-glucose and N-acetylglucosamine subunits are harvested and purified by washing with 1-6% aqueous NaOH with 1-4 cycles for 1-5 hrs total time. Pellicles are bleached with 0.1-1% $H_2O_2$ for 1-2 cycles for 1-2 hrs total time followed by soaking in multiple changes of distilled water until neutral pH is reached. Finally, the pellicles are mechanically pressed to the desired thicknesses.

The relative amounts of D-glucose and N-acetylglucosamine in the resulting exopolysaccharide is determined by LC-MS/MS after acid hydrolysis as described by Yadav, et al, 2010.

Example 3: Cloning and Expression of *Escherichia coli* Derived N-Acetylglucosamine Phosphoenolpyruvate-Dependent Sugar Phosphotransferase System Permease and *Candida albican* Derived N-Acetylglucosamine Metabolism Genes in *Komagataeibacter xylinus* and the Production of an Exopolysaccharide Containing D-Glucose and N-Acetylglucosamine The *Escherichia coli* nagE gene, *Candida albicans* nag5 gene (encoding N-acetylglucosamine kinase, EC:2.7.1.59), Candida albicans agm1 gene (encoding phosphoacetylglucosamine mutase, EC:5.4.2.3), and *Candida albicans* uap1 gene (encoding UDP-N-acetylglucosamine pyrophosphorylase, EC 2.7.7.23) are cloned into the expression vector pSEVA331 (GenBank: JX560333.1) under control of the LuxR promoter (Florea, et al 2016a). *K. xylinus* is transformed with the resulting plasmid as described by Florea, et al, 2016a and 2016b. Transformed bacteria are cultured in Erlenmeyer flasks filled with media for a period of 1-3 days at 30±2° C. as described in Example 1, above. The inoculated media with deposited pellicle is gently stirred and used as inoculum to conduct a larger-scale fermentation in tray reactors as described in Example 1, above, except the media in the tray reactors is further supplemented with 0.5-2% N-acetylglucosamine and 0.01-1 µM N-acyl homoserine lactone.

Pellicles of exopolysaccharide comprising D-glucose and N-acetylglucosamine subunits are harvested and purified by washing with 1-6% aqueous NaOH with 1-4 cycles for 1-5 hrs total time. Pellicles are bleached with 0.1-1% $H_2O_2$ for 1-2 cycles for 1-2 hrs total time followed by soaking in multiple changes of distilled water until neutral pH is reached. Finally, the pellicles are mechanically pressed to the desired thicknesses.

The relative amounts of D-glucose and N-acetylglucosamine in the resulting exopolysaccharide is determined by LC-MS/MS after acid hydrolysis as described by Yadav, et al, 2010.

Example 4: Cloning and Expression of *Escherichia coli* Derived N-Acetylglucosamine Phosphoenolpyruvate-Dependent Sugar Phosphotransferase System Permease and *Escherichia coli* and *Mus musculus* Derived N-Acetylglucosamine Metabolism Genes in *Komagataeibacter xylinus* and the Production of an Exopolysaccharide Containing D-Glucose and N-Acetylglucosamine The *Escherichia coli* nagE gene, *Escherichia coli* nagK gene (encoding GlcNac kinase), *Mus musculus* pgm3 gene (encoding phosphoacetyl-glucosamine mutase, EC:5.4.2.3), and *Escherichia coli* glmU gene (encoding bifunctional UDP-N-acetylglucosamine pyrophosphorylase/Glucosamine-1-phosphate N-acetyltransferase, EC:2.7.7.23 and 2.3.1.157) are cloned into the expression vector pSEVA331 (GenBank: JX560333.1) under control of the LuxR promoter (Florea, et al 2016a). *K. xylinus* is transformed with the resulting plasmid as described by Florea, et al, 2016a and 2016b. Transformed bacteria are cultured in Erlenmeyer flasks filled with media for a period of 1-3 days at 30±2° C. as described in Example 1, above. The inoculated media with deposited pellicle is gently stirred and used as inoculum to conduct a larger-scale fermentation in tray reactors as described in Example 1, above, except the media in the tray reactors is further supplemented with 0.5-2% N-acetylglucosamine and 0.01-1 µM N-acyl homoserine lactone.

Pellicles of exopolysaccharide comprising D-glucose and N-acetylglucosamine subunits are harvested and purified by washing with 1-6% aqueous NaOH with 1-4 cycles for 1-5 hrs total time. Pellicles are bleached with 0.1-1% $H_2O_2$ for 1-2 cycles for 1-2 hrs total time followed by soaking in multiple changes of distilled water until neutral pH is reached. Finally, the pellicles are mechanically pressed to the desired thicknesses.

The relative amounts of D-glucose and N-acetylglucosamine in the resulting exopolysaccharide is determine by LC-MS/MS after acid hydrolysis as described by Yadav, et al, 2010.

Example 5: Supercritical $CO_2$ ($sCO_2$) Drying

Cellulose sheets are extracted with ethanol or methanol by conducting a stepwise extraction: 30%, 50%, 90% (v/v) and absolute ethanol for 3 hours at each percentage. Samples are then dried using a Speed SFE supercritical $CO_2$ extraction system (Applied Separations, Inc., Allentown, Pa.) to maintain its open three-dimensional structure and nano-porosity.

Example 6: Manufacture of Resorbable Microbial-Derived Exopolysaccharide

This example is directed to a preparation of modified microbial-derived exopolysaccharide films produced by *K. xylinus* within a controlled environment to minimize bioburden (microorganism contamination). From a propagation vessel, sterilized media may be inoculated with *K. xylinus* expressing one or more of the exogenous enzymes described herein, filled into bioreactor trays and incubated until optimal growth of the pellicle is observed. The pellicles may be removed from the trays and then may undergo caustic chemical processing (depyrogenation) in a tank for about one hour. The pellicles then undergo a continuous rinse with filtered water. The films are compressed within a pneumatic press to yield a pellicle having a weight of approximately 4 to 10 g. Each unit is placed in a pouch, sealed, sterilized, and used for various tests, inclusive of exopolysaccharide content, endotoxin (LAL), and mechanical strength.

Example 7: Manufacture of Implantable Resorbable Microbial-Derived Exopolysaccharide for Hernia Mesh This example is directed to a preparation of modified microbial-derived exopolysaccharide films per the initial steps of Examples 1 and 2. Following chemical processing, the films are compressed within a pneumatic press to yield a pellicle having a weight of approximately 9 to 13 g. Each unit is placed in a closed container and decreased in temperature to below 0° C. After at least 24 hours, the temperature is increased to above freezing and excess moisture that is released is decanted to partially dehydrate the exopolysaccharide. The partially dehydrated material is placed in a pouch, sealed, sterilized, and used for various tests, inclusive of exopolysaccharide content, endotoxin (LAL), and mechanical strength.

It will be appreciated by those skilled in the art that various modifications and alterations of the invention can be made without departing from the broad scope of the appended claims. Some of these have been discussed above and others will be apparent to those skilled in the art.

The disclosures of each patent, patent application, and publication cited or described in this document are hereby incorporated herein by reference, in its entirety.

EMBODIMENTS

The following list of embodiments is intended to complement, rather than displace or supersede, the previous descriptions.

Embodiment 1

A microorganism for the production of an exopolysaccharide, wherein:
a. the microorganism expresses an exogenous enzyme, wherein the exogenous enzyme is N-acetylglucosamine phosphoenolpyruvate-dependent sugar phosphotransferase system permease or a biologically active homologue thereof; and
b. the microorganism produces an exopolysaccharide that comprises N-acetylglucosamine and D-glucose.

Embodiment 2

The microorganism of embodiment 1, wherein the microorganism further expresses at least one exogenous enzyme involved in N-acetylglucosamine uptake or metabolism.

Embodiment 3

The microorganism of embodiment 2, wherein the at least one exogenous enzyme involved in N-acetylglucosamine uptake or metabolism comprises one or more of N-acetylglucosamine kinase, phosphoacetyl-glucosamine mutase, or UDP-N-acetylglucosamine pyrophosphorylase.

Embodiment 4

The microorganism of embodiment 3, wherein the UDP-N-acetylglucosamine pyrophosphorylase also has glucosamine-1-phosphate N-acetyltransferase activity.

Embodiment 5

The microorganism of embodiment 3 or 4, wherein the N-acetylglucosamine kinase and/or the UDP-N-acetylglucosamine pyrophosphorylase are derived from a source other than yeast.

Embodiment 6

The microorganism of any one of the preceding embodiments, wherein the exogenous enzyme is encoded by a nucleic acid.

Embodiment 7

The microorganism of embodiment 6, wherein the nucleic acid is a cDNA molecule.

Embodiment 8

The microorganism of embodiment 6 or 7, wherein the nucleic acid is contained in a recombinant vector.

Embodiment 9

The microorganism of embodiment 8, wherein the recombinant vector is a viral or a plasmid vector.

Embodiment 10

The microorganism of any one of embodiments 6-9, wherein the nucleic acid is operably linked to a promoter.

Embodiment 11

The microorganism of embodiment 10, wherein the promoter is a constitutive or inducible promoter.

Embodiment 12

The microorganism of any one of the preceding embodiments, wherein the microorganism is a bacterium.

Embodiment 13

The microorganism of embodiment 12, wherein the bacterium belongs to the family Acetobacteraceae or a genus comprising *Agrobacterium, Aerobacter, Achromobacter, Azotobacter, Rhizobium, Sarcina,* or *Salmonella*.

Embodiment 14

The microorganism of embodiment 13, wherein the bacterium is *Komagataeibacter xylinus*.

Embodiment 15

A bacterium for the production of an exopolysaccharide, wherein:
a. the bacterium expresses at least one exogenous enzyme, wherein the at least one exogenous enzyme is N-acetylglucosamine kinase, yeast-derived phosphoacetyl-glucosamine mutase, or UDP-N-acetylglucosamine pyrophosphorylase; and
b. the bacterium produces an exopolysaccharide that comprises N-acetylglucosamine and D-glucose; and
wherein
the N-acetylglucosamine kinase and the UDP-N-acetylglucosamine pyrophosphorylase are derived from a source other than yeast, or
the N-acetylglucosamine kinase is derived from a source other than yeast and the UDP-N-acetylglucosamine pyrophosphorylase is derived from yeast, or
the N-acetylglucosamine kinase is derived from yeast and the UDP-N-acetylglucosamine pyrophosphorylase is derived from a source other than yeast.

Embodiment 16

The bacterium of embodiment 15, wherein the at least one exogenous enzyme is encoded by a nucleic acid.

Embodiment 17

The bacterium of embodiment 16, wherein the nucleic acid is a cDNA molecule.

Embodiment 18

The bacterium of embodiment 16 or 17, wherein the nucleic acid is contained in a recombinant vector.

Embodiment 19

The bacterium of embodiment 18, wherein the recombinant vector is a viral or a plasmid vector.

Embodiment 20

The bacterium of any one of embodiments 16-19, wherein the nucleic acid is operably linked to a promoter.

Embodiment 21

The bacterium of embodiment 20, wherein the promoter is a constitutive or inducible promoter.

Embodiment 22

The bacterium of any one of embodiments 15-21, wherein the bacterium belongs to the family Acetobacteraceae or a genus comprising *Agrobacterium*, *Aerobacter*, *Achromobacter*, *Azotobacter*, *Rhizobium*, *Sarcina*, or *Salmonella*.

Embodiment 23

The bacterium of embodiment 22, wherein the bacterium is *Komagataeibacter xylinus*.

Embodiment 24

A method for producing an exopolysaccharide comprising:
a. culturing a microorganism under conditions effective to produce the exopolysaccharide, and
b. recovering the exopolysaccharide,
wherein said microorganism expresses an exogenous enzyme, wherein the exogenous enzyme is N-acetylglucosamine phosphoenolpyruvate-dependent sugar phosphotransferase system permease or a biologically active homologue thereof, and wherein the exopolysaccharide comprises N-acetylglucosamine and D-glucose.

Embodiment 25

The method of embodiment 24, wherein the microorganism further expresses at least one exogenous enzyme involved in N-acetylglucosamine uptake and metabolism.

Embodiment 26

The method of embodiment 25, wherein the at least one exogenous enzyme involved in N-acetylglucosamine uptake and metabolism comprises one or more of N-acetylglucosamine kinase, phosphoacetyl-glucosamine mutase, or UDP-N-acetylglucosamine pyrophosphorylase.

Embodiment 27

The method of embodiment 26, wherein the UDP-N-acetylglucosamine pyrophosphorylase also has glucosamine-1-phosphate N-acetyltransferase activity.

Embodiment 28

The method of embodiment 26 or 27, wherein the N-acetylglucosamine kinase and/or the UDP-N-acetylglucosamine pyrophosphorylase are derived from a source other than yeast.

Embodiment 29

The method of any one of embodiments 24 to 28, wherein the microorganism is a bacterium.

Embodiment 30

The method of embodiment 29, wherein the bacterium belongs to the family Acetobacteraceae or a genus comprising *Agrobacterium*, *Aerobacter*, *Achromobacter*, *Azotobacter*, *Rhizobium*, *Sarcina*, or *Salmonella*.

Embodiment 31

The method of embodiment 30, wherein the bacterium is *Komagataeibacter xylinus*.

Embodiment 32

A method for producing an exopolysaccharide comprising:
a. culturing a bacterium under conditions effective to produce the exopolysaccharide, and
b. recovering the exopolysaccharide,
wherein said bacterium expresses at least one exogenous enzyme, wherein the at least one exogenous enzyme is N-acetylglucosamine kinase, yeast-derived phosphoacetyl-glucosamine mutase, or UDP-N-acetylglucosamine pyrophosphorylase, wherein the exopolysaccharide comprises N-acetylglucosamine and D-glucose, and wherein
the N-acetylglucosamine kinase and the UDP-N-acetylglucosamine pyrophosphorylase are derived from a source other than yeast, or
the N-acetylglucosamine kinase is derived from a source other than yeast and the UDP-N-acetylglucosamine pyrophosphorylase is derived from yeast, or
the N-acetylglucosamine kinase is derived from yeast and the UDP-N-acetylglucosamine pyrophosphorylase is derived from a source other than yeast.

Embodiment 33

The method of embodiment 32, wherein the bacterium belongs to the family Acetobacteraceae or a genus comprising *Agrobacterium*, *Aerobacter*, *Achromobacter*, *Azotobacter*, *Rhizobium*, *Sarcina*, or *Salmonella*.

Embodiment 34

The method of embodiment 33, wherein the bacterium is *Komagataeibacter xylinus*.

Embodiment 35

The method of any one of embodiments 24-34, wherein the microorganism or bacterium is cultured in a culture medium containing D-glucose, N-acetylglucosamine, glucosamine, 3-O-methylglucose, 2-deoxyglucose, or a combination thereof.

Embodiment 36

The method of any one of embodiments 24-35, further comprising the step of at least partially dehydrating the body of the exopolysaccharide.

Embodiment 37

The method of embodiment 36, wherein the step of at least partially dehydrating the body of the exopolysaccharide is performed by mechanical pressing.

Embodiment 38

The method of embodiment 36, wherein the step of at least partially dehydrating the body of the exopolysaccharide is performed by critical point drying using supercritical carbon dioxide.

Embodiment 39

The method of any one of embodiments 24-38, further comprising the step of contacting the exopolysaccharide with one or more active agents.

Embodiment 40

The method of any one of embodiments 36-39, further comprising the step of reacting the exopolysaccharide with an oxidizing agent.

Embodiment 41

The method of embodiment 40, wherein the oxidizing agent comprises metaperiodate, hypochlorite, dichromate, peroxide, permanganate, nitrogen dioxide, or a combination thereof.

Embodiment 42

The method of embodiment 41, wherein the oxidizing agent is sodium metaperiodate.

Embodiment 43

An implant for soft tissue repair, replacement, or augmentation comprising the exopolysaccharide produced by the method of any one of embodiments 24-42.

Embodiment 44

The implant of embodiment 43 for use in hernia repair, repair of dura mater, replacement of dura mater, or any combination thereof.

What is claimed:

1. A bacterium for the production of an exopolysaccharide comprising N-acetylglucosamine and D-glucose, wherein:
    the bacterium belongs to a genus comprising *Komagataeibacter, Agrobacterium, Aerobacter, Achromobacter, Azotobacter, Rhizobium, Sarcina,* or *Salmonella* and the bacterium expresses
    a. an *Escherichia coli* N-acetylglucosamine phosphoenolpyruvate-dependent sugar phosphotransferase system permease; and
    b. an *Escherichia coli* N-acetylglucosamine kinase, a *Mus musculus* phosphoacetyl-glucosamine mutase, and an *Escherichia coli* bifunctional UDP-N-acetylglucosamine pyrophosphorylase/glucosamine-1-phosphate N-acetyltransferase, and
    the bacterium produces an exopolysaccharide that comprises N-acetylglucosamine and D-glucose.

2. The bacterium of claim 1, wherein the bacterium is *Komagataeibacter xylinus*.

* * * * *